United States Patent
Muller

(10) Patent No.: US 10,092,393 B2
(45) Date of Patent: Oct. 9, 2018

(54) CORNEAL IMPLANT SYSTEMS AND METHODS

(71) Applicant: David Muller, Boston, MA (US)

(72) Inventor: David Muller, Boston, MA (US)

(73) Assignee: Allotex, Inc., Boston, MA (US)

( * ) Notice: Subject to any disclaimer, the term of this patent is extended or adjusted under 35 U.S.C. 154(b) by 492 days.

(21) Appl. No.: 14/152,425

(22) Filed: Jan. 10, 2014

(65) Prior Publication Data

US 2014/0264980 A1    Sep. 18, 2014

Related U.S. Application Data

(60) Provisional application No. 61/865,791, filed on Aug. 14, 2013, provisional application No. 61/864,021, filed on Aug. 9, 2013, provisional application No. 61/846,170, filed on Jul. 15, 2013, provisional application No. 61/786,115, filed on Mar. 14, 2013.

(51) Int. Cl.
*A61F 9/00* (2006.01)
*A61F 2/14* (2006.01)
*A61F 9/008* (2006.01)

(52) U.S. Cl.
CPC ............. *A61F 2/142* (2013.01); *A61F 2/145* (2013.01); *A61F 9/0081* (2013.01); *A61F 9/00812* (2013.01); *A61F 9/00831* (2013.01); *A61F 9/00834* (2013.01); *A61F 9/00836* (2013.01); *A61F 2009/0088* (2013.01); *A61F 2009/00844* (2013.01); *A61F 2009/00872* (2013.01); *A61F 2009/00882* (2013.01)

(58) Field of Classification Search
CPC ...... A61F 2/142; A61F 2/145; A61F 9/00812; A61F 9/00831; A61F 9/00834; A61F 9/00836
See application file for complete search history.

(56) References Cited

U.S. PATENT DOCUMENTS 2,302,918 A * 11/1942 Smith ................... B29B 11/02
                                                              264/1.1
4,646,720 A    3/1987 Peyman et al.
(Continued)

FOREIGN PATENT DOCUMENTS

CA    2650883    11/2007
EP    2371329 A1    10/2011
(Continued)

OTHER PUBLICATIONS

Hara et al., Xenotransplantation—The Future of Corneal Transplantation?
(Continued)

*Primary Examiner* — Mathieu D Vargot
(74) *Attorney, Agent, or Firm* — McDonnell Boehnen Hulbert & Berghoff LLP

(57) ABSTRACT

According to one aspect of the present disclosure, an implant for correcting vision impairment is disclosed. The implant is made from a donor corneal tissue sized and shaped to provide a predetermined refractive correction and reshaping of a cornea. The donor corneal tissue includes a posterior surface and an anterior surface. The posterior surface has a surface profile that is configured to generally correspond to a shape of an implantation site of the cornea.

15 Claims, 11 Drawing Sheets

(56) References Cited

U.S. PATENT DOCUMENTS

| | | |
|---|---|---|
| 4,764,930 A | 8/1988 | Bille et al. |
| 4,793,344 A | 12/1988 | Cumming et al. |
| 5,312,428 A | 5/1994 | Lieberman |
| 5,336,261 A | 8/1994 | Barrett et al. |
| 5,549,632 A | 8/1996 | Lai |
| 5,552,452 A | 9/1996 | Khadem et al. |
| 5,647,865 A * | 7/1997 | Swinger ............ A61F 9/008 128/898 |
| 5,702,414 A | 12/1997 | Richter et al. |
| 5,919,185 A | 7/1999 | Peyman |
| 5,993,438 A | 11/1999 | Juhasz et al. |
| 6,030,398 A | 2/2000 | Klopotek |
| 6,063,073 A | 5/2000 | Peyman |
| 6,099,541 A | 8/2000 | Klopotek |
| 6,197,019 B1 | 3/2001 | Peyman |
| 6,210,401 B1 | 4/2001 | Lai |
| 6,254,595 B1 | 7/2001 | Juhasz et al. |
| 6,280,470 B1 | 8/2001 | Peyman |
| 6,325,792 B1 | 12/2001 | Swinger et al. |
| RE37,585 E | 3/2002 | Mourou et al. |
| 6,436,092 B1 | 8/2002 | Peyman |
| 6,544,286 B1 | 4/2003 | Perez |
| 6,702,807 B2 | 3/2004 | Peyman |
| 6,949,093 B1 | 9/2005 | Peyman |
| 7,044,602 B2 | 5/2006 | Chernyak |
| 7,497,866 B2 | 3/2009 | Perez |
| 7,585,075 B2 | 9/2009 | Marmo |
| 7,611,507 B2 | 11/2009 | Raksi et al. |
| 7,776,086 B2 | 8/2010 | Miller |
| 7,828,844 B2 | 11/2010 | Marmo et al. |
| 7,883,520 B2 | 2/2011 | Gaeckle et al. |
| 7,973,079 B2 | 7/2011 | Mata et al. |
| 7,992,906 B2 | 8/2011 | Nigam |
| 8,057,541 B2 | 11/2011 | Dishler et al. |
| 8,092,490 B2 | 1/2012 | Redmond et al. |
| 8,162,953 B2 | 4/2012 | Dishler et al. |
| 8,240,850 B2 | 8/2012 | Apter et al. |
| 8,246,609 B2 | 8/2012 | Zickler et al. |
| 8,469,948 B2 | 6/2013 | Dishler et al. |
| 8,540,727 B2 | 9/2013 | Dishler et al. |
| 8,668,735 B2 | 3/2014 | Nigam et al. |
| 8,753,321 B2 | 6/2014 | Mrochen et al. |
| 8,784,406 B2 | 7/2014 | Rathjen |
| 8,845,624 B2 | 9/2014 | Raksi et al. |
| 8,900,296 B2 | 12/2014 | Holliday et al. |
| 8,949,093 B2 | 2/2015 | Degani et al. |
| 9,005,280 B2 | 4/2015 | Nigam |
| 9,271,828 B2 | 3/2016 | Schneider et al. |
| 9,345,569 B2 | 5/2016 | Plambeck et al. |
| 2001/0018612 A1 | 8/2001 | Carson et al. |
| 2003/0014042 A1 | 1/2003 | Juhasz et al. |
| 2003/0153904 A1 | 8/2003 | Patel |
| 2004/0243111 A1 | 12/2004 | Bendett et al. |
| 2005/0080484 A1 | 4/2005 | Marmo et al. |
| 2005/0125001 A1 | 6/2005 | Danon |
| 2006/0020259 A1 | 1/2006 | Baumeister et al. |
| 2006/0100612 A1 | 5/2006 | van der Heyd et al. |
| 2006/0116762 A1 | 6/2006 | Hong et al. |
| 2006/0134170 A1 | 6/2006 | Griffith et al. |
| 2006/0192921 A1 | 8/2006 | Loesel et al. |
| 2006/0276888 A1* | 12/2006 | Lee ............ A61F 2/2412 623/2.17 |
| 2007/0129797 A1 | 6/2007 | Lang et al. |
| 2007/0203577 A1 | 8/2007 | Dishler et al. |
| 2007/0208325 A1 | 9/2007 | Kurtz |
| 2007/0208422 A1 | 9/2007 | Walter et al. |
| 2007/0255401 A1 | 11/2007 | Lang |
| 2008/0033408 A1 | 2/2008 | Bueler et al. |
| 2008/0082086 A1 | 4/2008 | Kurtz et al. |
| 2008/0262610 A1 | 10/2008 | Lang et al. |
| 2008/0306573 A1 | 12/2008 | Campin et al. |
| 2009/0051876 A1 | 2/2009 | Seiler et al. |
| 2009/0118718 A1 | 5/2009 | Raksi et al. |
| 2010/0211051 A1 | 8/2010 | Weston et al. |
| 2010/0298443 A1 | 11/2010 | Widder et al. |
| 2011/0029073 A1 | 2/2011 | Liang |
| 2011/0290681 A1 | 12/2011 | Nigam |
| 2011/0294891 A1 | 12/2011 | Widder et al. |
| 2012/0108665 A1 | 5/2012 | Mata et al. |
| 2012/0202885 A1 | 8/2012 | Widder et al. |
| 2012/0203238 A1 | 8/2012 | Nigam |
| 2012/0288568 A1 | 11/2012 | Widder et al. |
| 2012/0309835 A1 | 12/2012 | Widder et al. |
| 2013/0041354 A1 | 2/2013 | Brownell et al. |
| 2013/0238091 A1 | 9/2013 | Danta et al. |
| 2014/0128821 A1 | 5/2014 | Gooding et al. |
| 2014/0142200 A1 | 5/2014 | Duan et al. |
| 2014/0200665 A1 | 7/2014 | Lang et al. |
| 2014/0232988 A1 | 8/2014 | Kersting et al. |
| 2014/0276677 A1 | 9/2014 | Brownell et al. |
| 2015/0080865 A1 | 3/2015 | Holliday et al. |
| 2015/0126970 A1 | 5/2015 | Thompson |
| 2015/0133901 A1 | 5/2015 | Serdarevic et al. |
| 2015/0168250 A1 | 6/2015 | Saxer et al. |
| 2015/0182331 A1 | 7/2015 | Blum et al. |
| 2015/0238308 A1 | 8/2015 | Ishak et al. |
| 2015/0250652 A1 | 9/2015 | Holliday et al. |
| 2015/0277145 A1 | 10/2015 | Bakaraju et al. |
| 2015/0366657 A1 | 12/2015 | Sharma |
| 2016/0022493 A1 | 1/2016 | Peyman |
| 2016/0062145 A1 | 3/2016 | Brennan et al. |
| 2016/0170232 A1 | 6/2016 | Wildsmith |
| 2016/0184085 A1 | 6/2016 | Schneider et al. |
| 2017/0115509 A1 | 4/2017 | Brennan et al. |

FOREIGN PATENT DOCUMENTS

| | | |
|---|---|---|
| RU | 2203006 C1 | 4/2003 |
| RU | 2470616 C1 | 12/2012 |
| WO | WO 93/08878 | 5/1993 |
| WO | WO 94/09849 | 5/1994 |
| WO | WO 03/075778 | 9/2003 |
| WO | WO 2004/028357 | 4/2004 |
| WO | WO 2006/011011 | 2/2006 |
| WO | WO 2007/143111 | 12/2007 |
| WO | WO 2008/030699 | 3/2008 |
| WO | WO 2008/060810 | 5/2008 |
| WO | WO 2008/131888 | 11/2008 |
| WO | WO 2009/146151 | 12/2009 |
| WO | 2011152861 A2 | 12/2011 |
| WO | WO 2012/035403 | 3/2012 |
| WO | WO 2012/170966 | 12/2012 |
| WO | 2013159798 A1 | 10/2013 |
| WO | WO 2015/003779 | 1/2015 |
| WO | WO 2015/183941 | 12/2015 |

OTHER PUBLICATIONS

Miclea et al., Applanation-Free Femtosecond Laser Processing of the Cornea.

Moore et al., Fate of Lyophilized Xenogeneic Corneal Lenticules in Intrastromal Implantation and Epikeratophakia.

Shaw, Eyelid Pressure on the Cornea, p. 107-143.

Smith et al., Effect of Defocus on on-axis Wave Aberration of a Centered Optical System.

Studer et al., Biomechanical Modeling of Femtosecond Laser Keyhole Endokeratophakia Surgery.

Whitford et al., Biomechanical Model of the Human Corena: Considering Shear Stiffness and Regional Variation of collagen Anisotropy and Density.

International Search Report for corresponding PCT International Patent Application No. PCT/US2014/028103, dated Jul. 16, 2014 (3 pages).

Written Opinion of the International Searching Authority for corresponding PCT International Patent Application No. PCT/US2014/028103, dated Jul. 16, 2014 (5 pages).

European Search Report for corresponding European Patent Application No. 14769291.7, dated Mar. 29, 2017 (10 pages).

* cited by examiner

CORNEAL IMPLANT SYSTEMS AND METHODS

CROSS REFERENCE TO RELATED APPLICATIONS

This application claims priority to and the benefit of U.S. Provisional Application No. 61/865,971, filed Aug. 14, 2013, U.S. Provisional Application No. 61/864,021, filed Aug. 9, 2013, U.S. Provisional Application No. 61/846,170, filed Jul. 15, 2013, and U.S. Provisional Application No. 61/786,115, filed Mar. 14, 2013, the contents of these applications being incorporated entirely herein by reference.

FIELD OF THE INVENTION

The present invention relates generally to systems and methods for correcting vision, and more particularly, to systems and methods that employ eye implants to reshape the cornea in order to correct vision.

BACKGROUND

Presbyopia is a condition in which the crystalline lens of the eye loses its ability to focus on and see objects that are closer to the eye. In general, the lens needs to change its shape to focus on objects that are closer to the eye. The ability of the lens to change shape is known as the elasticity of the eye. As people age, the lens slowly loses its elasticity in a natural process. This results in a slow decrease in the ability to focus on nearby objects. Typically, presbyopia is addressed through the use of reading glasses, bifocals, trifocals, or contact lenses.

Figure 1A:
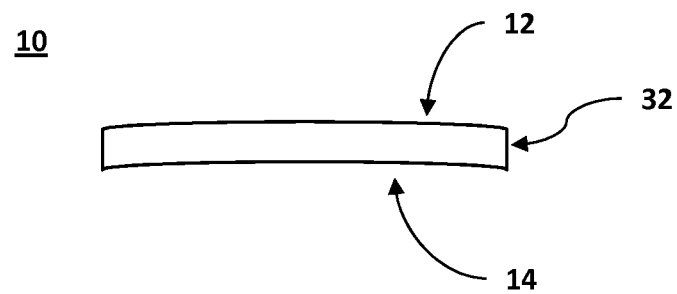
FIGS. 1A-1B illustrate an exemplary eye implant formed from natural tissue according to aspects of the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DESCRIPTION

Embodiments according to aspects of the present invention provide systems and methods that produce and employ eye implants to reshape the cornea in order to correct vision. In particular, such embodiments may address the loss of near vision associated with presbyopia described above. However, the eye implants contemplated in the present invention also may be employed to address other disorders of the eye.

In some embodiments, systems and methods employ eye implants that are formed from natural tissue. For example, the eye implants may be formed as allografts (i.e., tissue that is transplanted between members of the same species) or as xenografts (i.e., tissue that is transplanted between members of different species). More particularly, for example, the eye implants may be formed from donor corneal tissue. According to some aspects of the present disclosure, the eye implants can be precisely manufactured according to patient specific conditions. For example, the eye implants of the present disclosure can be manufactured to have a shape that generally corresponds to a shape of an implantation site of the patient's cornea, provides a predetermined amount of refractive correction, and/or addresses corneal irregularities.

It has been discovered that the methods and eye implants of the present disclosure exhibit significant improvements over prior attempts to correct vision utilizing eye implants. For example, some prior attempts to correct vision utilized eye implants made from synthetic materials; however, such eye implants made from synthetic materials did not work well for a variety of reasons (e.g., the irregularity of the collagen matrix of an eye, differences in the state of hydration of the synthetic material and the collagen matrix of an eye, lack of biocompatibility, etc.). The methods and eye implants of the present disclosure, which are made from natural tissue, overcome the deficiencies of such prior attempts. In particular, for example, the methods and eye implants of the present disclosure, which are made from natural tissue, exhibit greater biocompatibility with a patient's cornea, more closely match the index of refraction of the patient's cornea, can be maintained at a state of hydration that is required for implantation (e.g., a state of hydration that is similar to that of the implantation site), and ensures that sufficient gas and nutrients can be exchanged within the patient's cornea. Such advantages have not been achieved or successfully commercialized, at least in part, due to a lack of suitable methods and systems for manufacturing eye implants made from natural tissue.

Figure 1B:
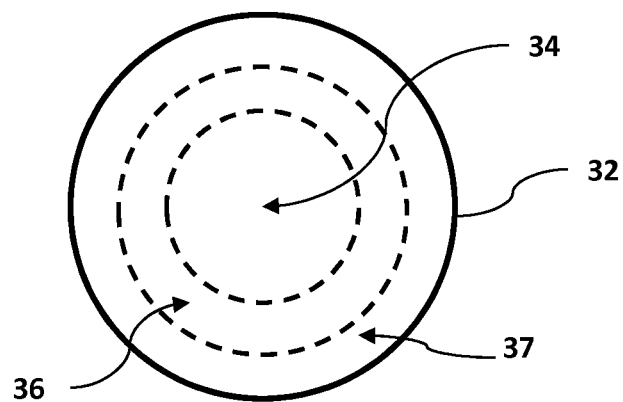

FIGS. 1A and 1B illustrate an exemplary eye implant 10 according to aspects of the present disclosure. The eye implant 10 is formed from natural tissue or, more particularly, for example, a donor cornea. As shown in FIG. 1A, the eye implant 10 has a front surface 14 (i.e., an anterior-implant surface 12) and a back surface 12 (i.e., a posterior-implant surface 14). While the exemplary eye implant 10 illustrated in FIG. 1 has a front surface 14 and back surface 12 that form a meniscus shape, according to other aspects of the present disclosure, the eye implant 10 can have a plano-convex shape, a plano-concave shape, a bi-convex shape, or the like. Additionally, the front surface 14 and/or the back surface 12 can be spherical and/or aspherical.

To facilitate a description of some aspects of the eye implants 10, FIG. 1B shows a top plan view of the eye implant 10 having a central region 34, a mid-peripheral region, 36, an outer peripheral region 37, and a peripheral edge 32; however, it should be understood that such regions 34, 36, 37 are intended as one non-limiting example and the implants 10 can have any number (i.e., one or more) of regions of any size. Additionally, while the exemplary eye implant 10 illustrated in FIGS. 1A and 1B has a circular perimeter shape defined by the peripheral edge 32, according to other aspects of the present disclosure, the eye implant 10 can have an oval shape, a polygonal shape, a non-polygonal shape, or the like.

As will be described in further detail below, according to aspects of the present disclosure, the back surface 12 of the eye implant 10 can be shaped to have a surface profile that generally corresponds to a surface profile of an implantation site of a patient's cornea and the front surface 14 of the eye implant 10 can be shaped to have a surface profile that provides a predetermined refractive correction. To achieve this, the eye implant 10 can be precisely manufactured according to conditions specific to the patient in whom the eye implant 10 is to be implanted. A commercially viable method of manufacturing such eye implants 10 made from natural tissue has not previously been achieved.

Figure 2:
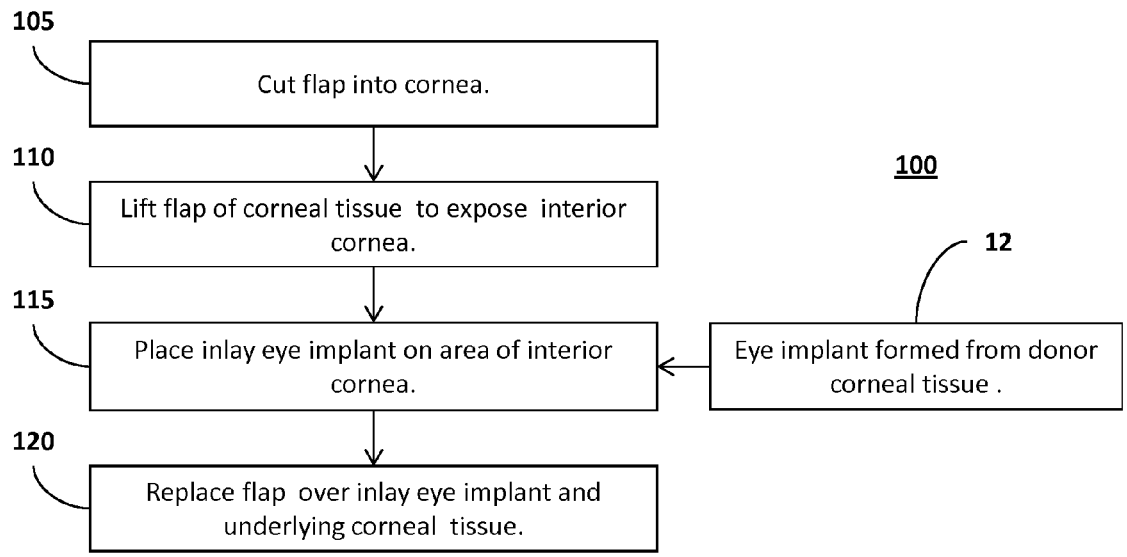
FIG. 2 illustrates an example procedure employing an inlay eye implant formed from natural tissue, according to aspects of the present invention.

FIG. 2 illustrates an example procedure 100 for implantation of the eye implants 10 according to some aspects of the present invention. In step 105, a flap is formed in a cornea 16. For example, a laser (e.g., a femtosecond laser), a mechanical keratome, other cutting mechanisms (e.g., a blade), etc., may be used to cut the flap. In some embodiments, the flap may be as thin as flaps that are cut for Sub-Bowman's Keratomileusis. The flap is sufficiently large to provide stability and ease of handling. In step 110, the flap of corneal tissue is lifted to expose the corneal interior 18. Thus, as a result of step 105 and step 110, an anterior portion 20 of the cornea 16 is separated from a posterior portion 22 of the cornea 16 to expose a stromal bed 24 upon which the implant 10 can be implanted.

In step 115, the eye implant 10 formed from donor corneal tissue is placed onto the stromal bed 24 at an implantation site in the exposed interior area 18 of the cornea 16 formed in step 105. The back surface 12 of the implant 10 is placed into contact with the bed 24 and may have a shape that corresponds to the shape of the bed 24 at the implantation site. In some cases, the back surface 12 of the implant 10 may have a non-flat surface curvature that generally corresponds to the non-flat curvature of the bed 24 at the implantation site. Alternatively, the back surface 12 of the implant 10 may be generally flat to correspond with a generally flat bed 24 at the implantation site.

According to some aspects, the eye implant 10 is implanted into the cornea 16 in a hydrated state. In some cases, the implant 10 can be transferred, via an insertion device (not shown), from a storage media containing the implant 10 prior to the procedure 100 to the implantation site. In other cases, the implant 10 can be transferred from a controlled environment directly and immediately to the implantation site. For example, the insertion device can be configured to maintain the implant 10 in the desired hydrated state. In step 120, the flap is replaced over the eye implant 10 and corneal interior 18. With the flap in place after step 120, the cornea 16 heals and seals the flap of corneal tissue to the rest of the cornea 16 (i.e., the anterior portion 20 seals to the posterior portion 22 to enclose the implant 10).

Figure 3:
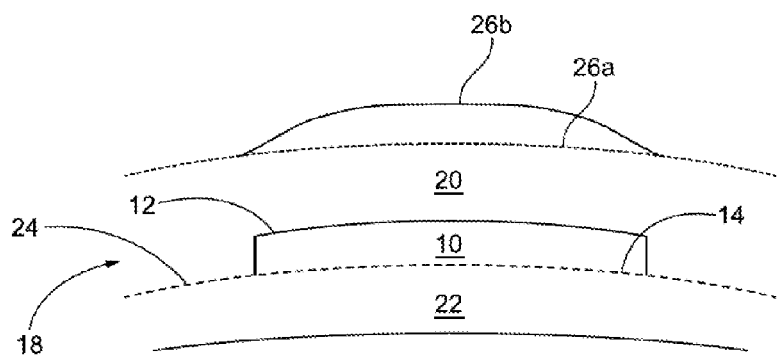
FIG. 3 illustrates an inlay implanted within corneal tissue, according to aspects of the present invention.

As shown in FIG. 3, after the procedure 100, the eye implant 10 is surgically inserted within the interior 18 of the cornea 16 with an anterior portion 20 of corneal tissue 16 disposed over the eye implant 10. Accordingly, in FIGS. 2-3, the implant 10 is implanted as an inlay implant because it is surgically implanted within the interior 18 of the cornea 16 (i.e., between the anterior portion 20 and a posterior portion 22 of the cornea 16). The eye implant 10 changes the shape of the cornea 16 as evidenced by a change in the anterior corneal surface 26A, 26B (e.g., in FIG. 3, the anterior corneal surface is shown as a dashed line 26A prior to the implantation and as a solid line 26B after implantation). This change in shape of the anterior corneal surface 26A, 26B results in corrective modification of the cornea 16, e.g., refractive correction. For example, the eye implant 10 may address the loss of near vision associated with presbyopia. To correct the effects of presbyopia, the eye implant 10 may be sized and positioned so that the change to the corneal shape improves near vision while having minimal effect on distance vision, which requires no correction. In general, however, the eye implants 10 may have any size or shape to produce the necessary desired correction. For example, in some cases, the implant 10 may have a diameter of up to approximately 10 mm, but preferably not more than approximately 7 mm.

While the eye implant 10 shown in FIG. 3 is employed as an inlay eye implant 10, it is understood that applying the eye implant 10 to the cornea 16 is not limited to the procedure 100 described above and that other procedures may be employed. For example, rather than forming a flap, a pocket having side walls with an opening may be formed (e.g., with a femtosecond laser or other cutting mechanism) to receive the implant 10. Stated more generally, the cornea 16 can be cut to separate the anterior portion 20 of the cornea 16 (e.g., the flap or an anterior section of a pocket) from the posterior portion 22 of the cornea 16, exposing the corneal interior 18 upon which the eye implant 10 can then be placed at an implantation site and subsequently covered by the anterior portion 20 of the cornea 16.

Figure 4A:
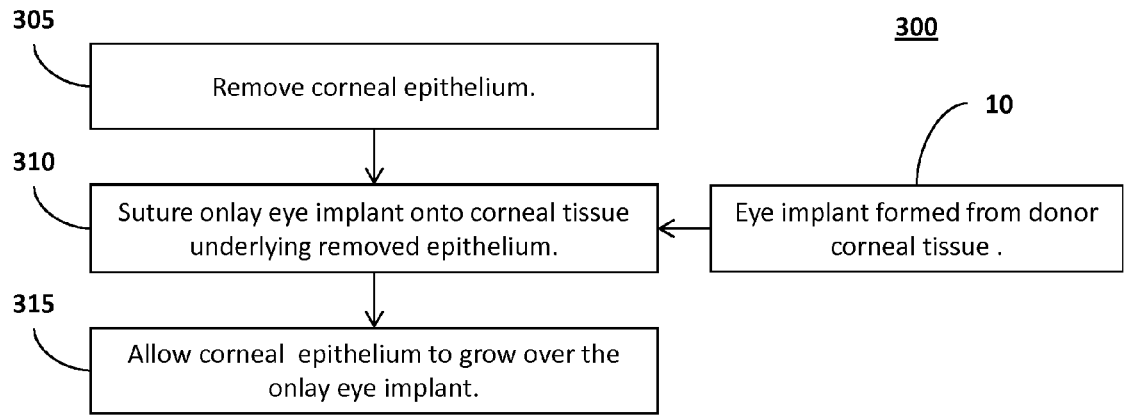
FIG. 4A illustrate an example procedure employing an onlay eye implant formed from natural tissue, according to aspects of the present invention.

In other embodiments, the eye implant 10 may be employed as an onlay eye implant, where it is placed on an outer portion 28 of the cornea 16 just under the epithelium 30 so that the epithelium 30 can grow over the eye implant 10. For example, in an exemplary procedure 300 shown in FIG. 4A, at least a portion of the epithelium 30 is removed (e.g., scraped) from the cornea 16 in step 305 and the eye implant 10 is sutured over the outer portion 28 of the corneal tissue 16 in step 310 where the epithelium 30 is allowed to grow over the eye implant 10 in step 315.

Figure 4B:
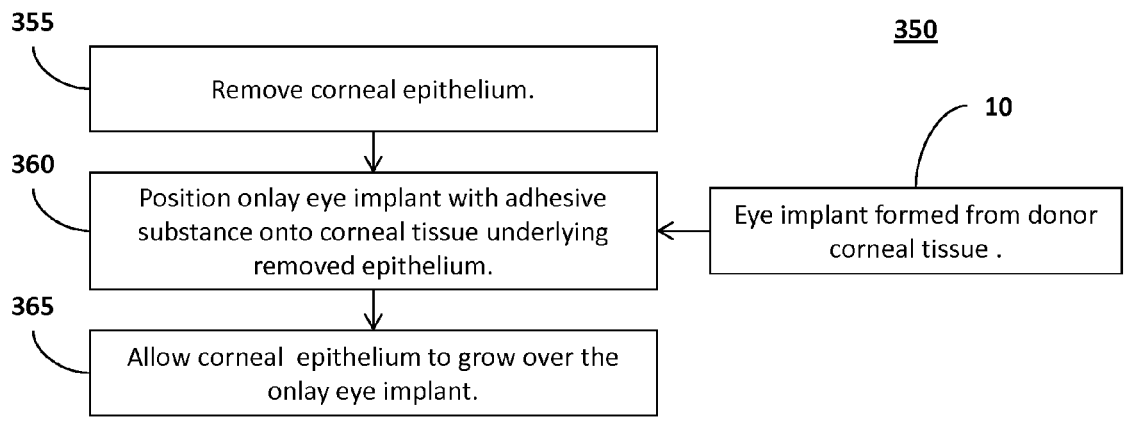
FIG. 4B illustrate another example procedure employing an onlay eye implant formed from natural tissue, according to aspects of the present invention.

Alternatively, in another exemplary procedure 350 shown in FIG. 4B, at least a portion of the epithelium 30 is removed (e.g., scraped) from the cornea in step 355 and the eye implant 10 is stably positioned with an adhesive substance over the outer portion 28 of the corneal tissue 16 in step 360 where the epithelium 30 is allowed to grow over the eye implant 10 in step 365. The adhesive substance, for example, may be a synthetic, biocompatible hydrogel that creates a temporary, soft, and lubricious surface barrier over the eye implant 10, keeping the eye implant 10 in place for the growth of the epithelium 30. According to some aspects of the present disclosure, the adhesive substance can include a cross-linking agent, as will be described in further detail below. In one non-limiting example, the onlay implant 10 can be dipped into riboflavin to facilitate assist in visualizing placement of the implant 10 on the outer portion 28 of the cornea 16. After placement onto the outer portion 28, the cross-linking agent can be activated (e.g., via a photoactivating light) to hold the implant 10 accutely to the outer portion 28 of the cornea 16.

Figure 5:
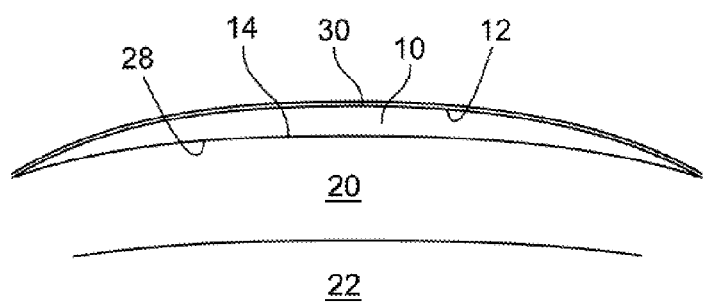
FIG. 5 illustrates an onlay implanted under corneal epithelium, according to aspects of the present invention.

Like the inlay eye implant, the onlay eye implant changes the shape of the cornea 16 and results in corrective modification of the cornea 16. Thus, the onlay eye implant may be applied to treat all refractive errors. As shown in FIG. 5, after the procedures 300 or 350, the corneal epithelium 30 grows over the eye implant 10 which is implanted on the outer portion 28 of the corneal tissue 16. The epithelium 30 is generally about 50 micrometers (i.e., 5-6 cell layers) thick and generally regenerates when the cornea 16 is damaged or partially removed. To facilitate recovery after implantation, the shape of the eye implant 10 is configured to facilitate the advancement of the epithelium 30 smoothly over the eye implant 10 during regeneration. More particularly, the eye implant 10 can have a tapered profile at the outer peripheral region 37 such that the implant 10 becomes thinner from the mid-periphery region 36 towards the peripheral edge 32 of the eye implant 10. Formed from donor corneal tissue, the eye implant 10 advantageously promotes effective growth of the epithelium 30. In addition, the eye implant 10 provides the accuracy required to achieve the desired correction in the eye.

As described above, the onlay eye implant 10 is implanted on an outer portion 28 of the cornea 16 under the corneal epithelium 30. According to some aspects, the onlay eye implant 10 can be implanted between the Bowman's membrane and the epithelium 30. According to additional and/or alternative aspects, the onlay eye implant 10 can be implanted between one or more cell layers of the epithelium 30. According to still other additional and/or alternative aspects, the onlay implant 10 can be implanted such that a minor portion penetrates the Bowman's membrane and/or the stroma so long as a major portion of the onlay implant 10 is located on or above the Bowman's membrane and under the outermost layer of the epithelium 30.

According to some aspects of the present disclosure, the eye implant 10 (i.e., as an inlay or as an onlay) can be shaped to accommodate a single zone of power for vision correction. As a non-limiting example, the implant 10 can be shaped primarily to accommodate near-vision. As another non-limiting example, the implant 10 can be shaped to accommodate mid-vision or far-vision. According to other aspects of the present disclosure, the implant 10 can be shaped to provide multi-focality, e.g., accommodate more than one zone of different power. For example, the implant 10 can include a plurality of different portions that are each shaped to accommodate a different zone of power. While the eye implant 10 illustrated in FIG. 1 is described as having a central region 34, a mid-peripheral region 36, and an outer peripheral region 37, it should be understood that the eye implant 10 can have any other number of regions, each having a different power. As one non-limiting example, the central region 34 of the implant 10 may be shaped to accommodate near-vision, the mid-peripheral region 36 of the implant 10 may be shaped to accommodate mid-vision, and/or the outer peripheral region 37 of the implant 10 may be shaped to accommodate far-vision.

Figure 6:
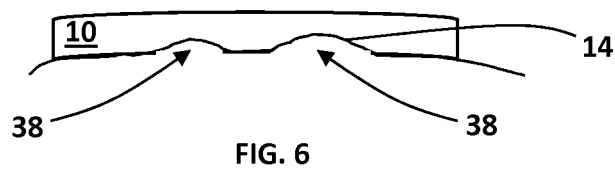
FIG. 6 illustrates an exemplary implant for addressing surface irregularities, according to aspects of the present invention.
Figure 7A:
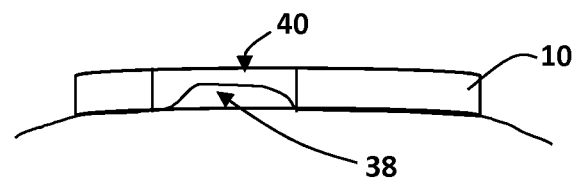
FIGS. 7A-7B illustrate another exemplary implant for addressing surface irregularities, according to aspects of the present invention.
Figure 7B:
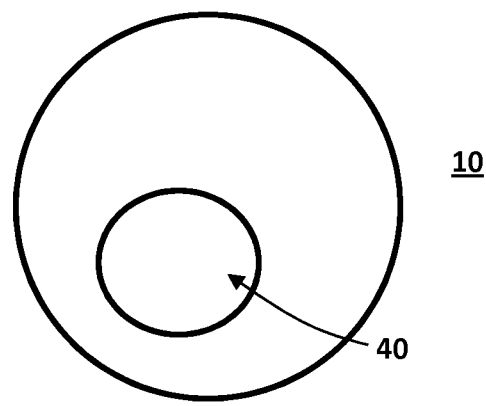

In some cases, patients with ectasia or keratoconus, for example, have corneal surface irregularities. Because their corneas 16 are typically thinner than normal, ablation techniques cannot be employed to smooth the shape of the corneas 16 to a more regular shape. To address this problem, a custom implant 10 (i.e., an inlay or an onlay) may be formed to have a shape that is generally the inverse of the surface irregularity and thus compensates for the surface irregularity. The implant 10 may be formed to have a front surface 14 that generally reproduces the back surface 12 curvature. For example, the implant 10 may be relatively thinner over areas of the cornea 16 that are relatively higher (i.e., extend outwardly), and vice versa. A non-limiting example of an onlay implant 10 that having a back surface 12 that is the inverse of the surface irregularities 38 of the outer portion 28 of the cornea 16 is illustrated in FIG. 6. The implant 10 may even have an aperture 40 that is positioned over steep and high portions of the cornea 16. For example, FIGS. 7A-7B illustrate a non-limiting example of an onlay implant 10 having an aperture 40 over a steep and high portion 42 of the outer portion 28 of the cornea 16. The implant 10 may be implanted as an inlay or an onlay according to the techniques described above.

It should be understood that the procedures 100 and 200 described above can include additional steps and/or the steps can be modified. For example, according to some aspects of the present disclosure, one or more cross-linking agents may be applied to the eye implants 10 to strengthen or stiffen them before they are implanted. In other embodiments, one or more cross-linking agents may be employed to stabilize the patient's cornea 16 after the eye implants 10 are implanted. In yet further embodiments, the cross-linking agents may be employed as an adhesive substance to hold the eye implant 10 stably in place for the implant procedures. For example, in the example procedure 350 above, an onlay eye implant 10 may be dipped into a cross-linking agent and the onlay eye implant 10 is held stably in place for subsequent growth of the epithelium 30 by the cross-linking that occurs with surrounding corneal tissue 16. In some cases, the application of cross-linking agent allows the eye implant 10 to be more easily visualized for the implant procedure.

The cross-linking agents that may be employed according to aspects of the present invention include, but are not limited to, Riboflavin, Rose Bengal, or Glutaraldehyde. For example, a dose of Ribloflavin may be applied topically and photoactivating light, such as ultraviolet (UV) light, may be applied to the Riboflavin to initiate cross-linking. Similarly, a dose of Rose Bengal may be applied topically and photoactivating light, such as visible, e.g., green, light, may be applied to the Rose Bengal to initiate cross-linking. The photoactivating light initiates cross-linking activity by causing the applied Riboflavin or Rose Bengal to release reactive radicals, such as singlet oxygen, in the corneal tissue. It is understood however, that aspects of the present invention do not require the application of a cross-linking agent.

Figure 8:
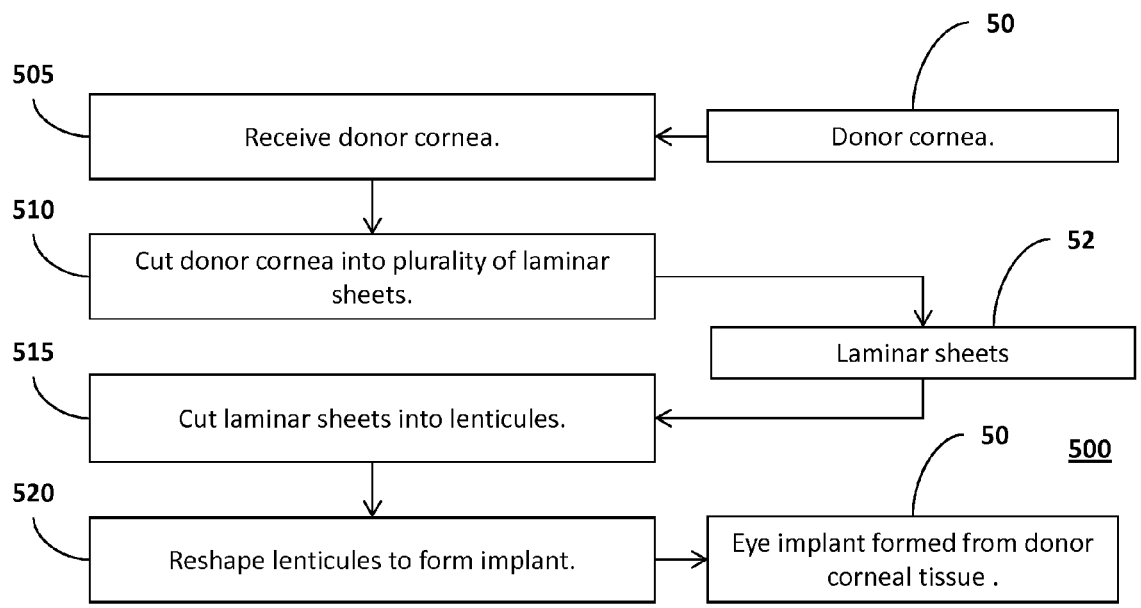
FIG. 8 illustrates an example procedure for processing donor corneal tissue to produce an eye implant, according to aspects of the present invention.
Figure 9A:
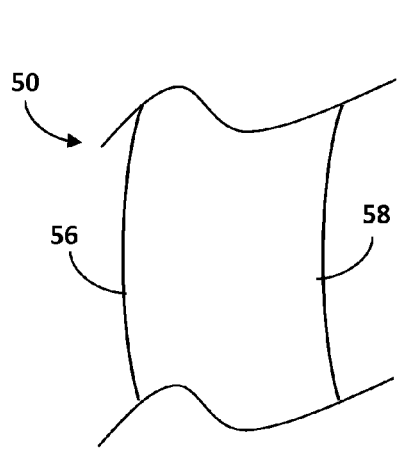
FIGS. 9A-9B illustrate a partial sectional view of an example donor cornea cut into laminar sheets, according to aspects of the present invention.
Figure 9B:
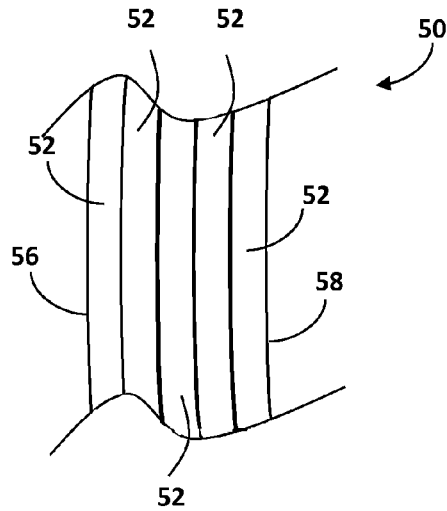

Referring to FIG. 8, an example procedure 500 for processing a donor cornea to manufacture one or more eye implants 10 is illustrated according to aspects of the present disclosure. In step 505, a donor cornea 50 is received. In step 510, the donor cornea 50 is cut into a plurality of laminar sheets 52. In some embodiments, for example, the laminar sheets 52 may have a thickness of approximately 10 μm to approximately 50 μm; however, it should be understood that the laminar sheets 52 can have other thicknesses. To further illustrate, a partial cross-section of the donor cornea 50 is shown in FIG. 9A prior to the cutting in step 510 and in FIG. 9B after the laminar sheets 52 have been cut from the donor corneal tissue 50 in step 510. As shown in FIGS. 9A-9B, the laminar sheets 52 can be cut such that the thickness of each laminar sheet 52 is measurable in a direction from an anterior surface 56 of the donor cornea 50 to a posterior surface 58 of the donor cornea 58.

Figure 10:
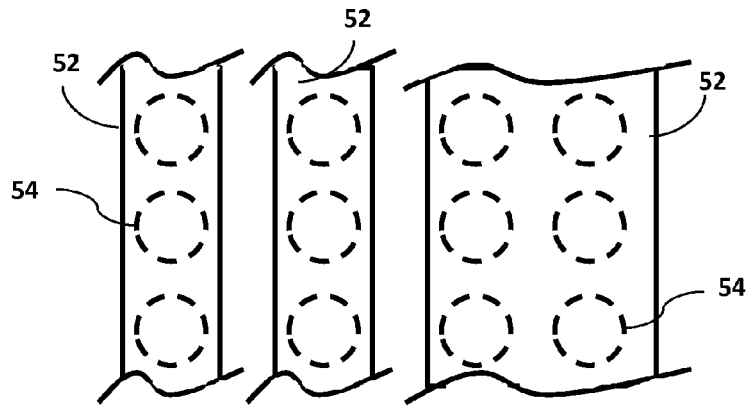
FIG. 10 illustrates an example of a plurality of lenticules to be cut from a plurality of laminar sheets, according to aspects of the present invention.

In step 515, one or more lenticules 54 are cut from each of the laminar sheets 50. For example, FIG. 10 shows portions of a plurality of laminar sheets 52 from which one or more lenticules 54 may be cut along the indicated dashed lines. In the illustrated example, the lenticules 54 are each configured to be cut as a disc-shaped piece of corneal tissue 50; however, according to additional and/or alternative aspects of the present disclosure, the one or more lenticules 54 can be cut from the laminar sheet 52 according to other perimeter shapes (e.g., a circular shape, an oval shape, a polygonal shape, a non-polygonal shape, or the like).

In step 520, the one or more lenticules 54 are further reshaped for corrective purposes to produce the eye implants 10. For example, the surfaces of each lenticule 54 can be reshaped (e.g., via cutting and/or ablation) to form an implant 10 having a predetermined size, perimeter shape, thickness, front surface 14 profile, and/or back surface 12 profile to produce the necessary desired correction, e.g., refractive correction. In one exemplary implementation, the lenticules 54 can be cut from the laminar sheets 52 in the predetermined size and perimeter shape at step 515 and the implant 10 can be formed by reshaping the front surface 14 and the back surface 12 at step 520. In another exemplary implementation, the lenticules 54 can be cut from the laminar sheets 52 with a first size and/or a first perimeter shape at step 515 and then reshaped at step 520 to have a second size and/or a second perimeter shape, which are different from the first size and first shape, in addition to reshaping the front surface 14 and the back surface 12 at step 520.

The precise cutting and shaping of the eye implants 10 in the procedure 500 can be achieved, for example, by a femtosecond laser, an excimer laser, and/or other cutting mechanisms (e.g., a blade, a clawer, a mechanical keratome, etc.). In one non-limiting example, the laminar sheets 52 are cut from the donor cornea 50 using a femtosecond laser in step 510 and the lenticules 54 are reshaped to form the implants 10 using an excimer laser in step 520. Advantageously, the procedure 500 precisely processes donor corneal tissue to produce a plurality of eye implants 10 from a single donor cornea 50. As will be described in further detail below, aspects of the procedure 500 can be automated. For example, an automated system can manipulate the lenticules 54 by machine in a "pick and pack" process. Using the laminar sheets 52 facilitates this automated manipulation by the machine.

According to some aspects of the present disclosure, all of the plurality of implants 10 that are produced from a single donor cornea 50 can have the same shape and/or size. However, according to additional and/or alternative aspects of the present disclosure, the plurality of implants 10 can be produced from the single donor cornea 50 in one or more different shapes and/or sizes. As will be described in further detail below, each of the eye implants 10 resulting from the procedure 500 can be custom produced for a specific individual patient (i.e., based on patient specific conditions) and/or the eye implants 10 can be produced with shapes and dimensions determined to be suitable for one or more different groups of individuals (e.g., similar to how contact lenses are manufactured in different sizes and optical powers for different groups of individuals).

Figure 11:
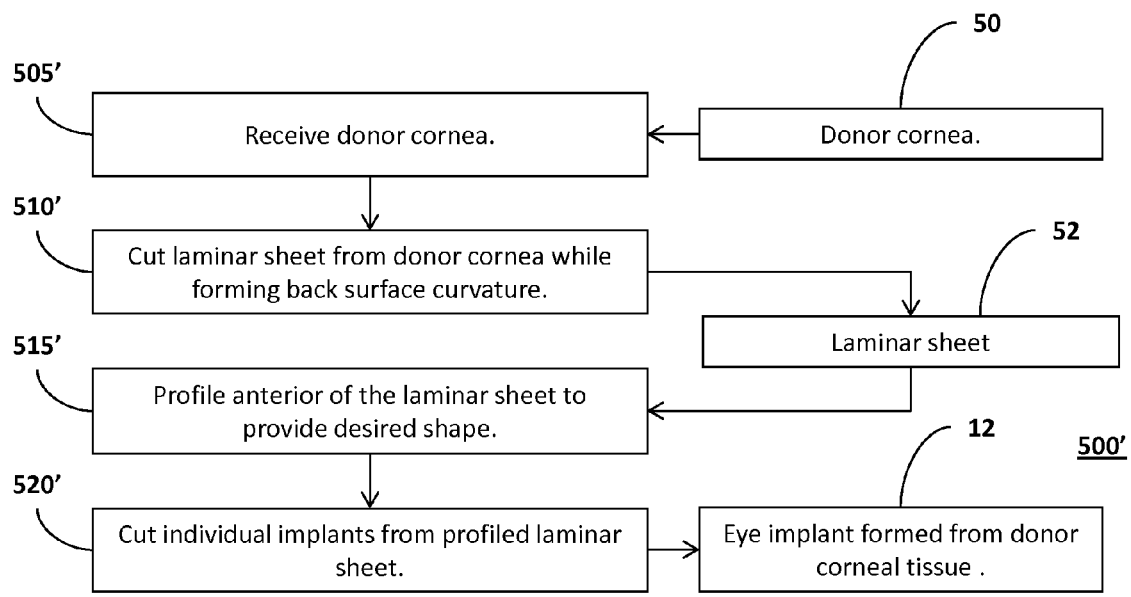
FIG. 11 illustrates another example procedure for processing corneal tissue to produce an eye implant, according to aspects of the present invention.

It should be understood that the procedure 500 for manufacturing the eye implants 10 described above can include additional steps and/or the steps can be modified. For example, FIG. 11 illustrates an example of a modified procedure 500' for processing a donor cornea 50. In step 505', a donor cornea 50 is received. In step 510', a laminar cut 52 is made from the donor cornea 50 while simultaneously forming the desired back surface 12 curvature. In step 515', the front surface 14 of the laminar sheet 52 is profiled to provide the desired shape, e.g., radius of curvature. In step 520', individual implants 10 are cut from the laminar sheet 52 which has been profiled. As another example, the reshaping of the front surface 14 and the back surface 12 can be formed on the laminar sheet 52 at step 515' such that when the implant 10 is formed when the lenticule 54 is cut from the laminar sheet at step 520'.

According to additional and/or alternative aspects of the present disclosure, the procedure 500 can be conducted in a controlled environment so that the corneal tissue 50 is maintained in the same state of hydration that is required for implantation. For example, the procedure 500 can include an additional step of submerging the donor corneal tissue 50 in a fluid such that one or more of the steps 510, 515, and/or 520 of the procedure 500 described above can be performed while the donor corneal tissue 50 is submerged in the fluid. As non-limiting examples, the fluid can include dextran sulfate sodium (DSS), optisol, a liquid preservative, combinations thereof, and/or the like. According to additional and/or alternative aspects of the present disclosure, the procedure 500 can include an additional step of drying the donor corneal tissue 50, the laminar sheets 52, and/or the lenticules 54 to facilitate the cutting and/or reshaping described above for steps 510, 515, and 520. According to one non-limiting example, the lenticules 54 can be slightly dried prior to the reshaping at step 520. According to additional and/or alternative aspects of the present disclosure, the procedure 500 can include an additional step to applanate the laminar sheet 52 and/or the lenticules 54 to facilitate the cutting and/or the reshaping in step 515 and/or step 520.

According to other additional and/or alternative aspects, the procedure 500 can include an additional step of applying a cross-linking agent to the donor cornea 50 to strengthen or stiffen the corneal tissue 50 for manipulation, cutting, and/or reshaping. The procedure 500 can also include a step for activating the cross-linking agent (e.g., by applying photo-activating light) to initiate cross-linking in the donor cornea 50, the laminar sheets 52, the lenticules 54, and/or the formed eye implant 10. According to still other additional and/or alternative aspects, the procedure 500 can include one or more additional steps for sterilizing the donor cornea 50, the laminar sheets 52, the lenticules 54, and/or the produced implants 10. As one non-limiting example, the step of sterilizing can include gamma ray radiation. It should be understood that the step of sterilizing can be conducted one or more times before, during, and/or after any step of the procedure 500 (e.g., before and after the reshaping at step 520). As described above, the procedure 500 can also include a step of transferring the eye implant 10 to a storage media according to additional and/or alternative aspects. In some embodiments, the storage media can be configured to maintain the eye implant 10 in the state of hydration that is necessary for subsequent implantation of the eye implant 10 in a patient's cornea 16. Alternatively, the eye implant 10 can be implanted in the cornea 16 directly after the eye implant 10 is produced from the procedure 500.

According to additional and/or alternative aspects, the procedure 500 can include an additional step of measuring one or more patient conditions to assist in obtaining an appropriate refractive correction specific to the patient in which the eye implant 10 is to be implanted. For example, a patient-measurement device can be employed to obtain information about the patient's cornea 16 in the form of aberration wavefront measurements, corneal topography measurements, pachymetry measurements, combinations thereof, and/or the like. Based on such measurements, the eye implant 10 to be implanted in the cornea 16 can be selected from a set of different eye implants 10 previously manufactured according to a plurality of different predetermined configurations and/or custom manufactured based on the patient specific information. That is, according to some embodiments, the eye implant 10 can be manufactured first and then selected based on the patient specific information obtained via the patient-measurement device. In such embodiments, the eye implants 10 can be mass produced according to the different predetermined configurations and then stored onsite in storage media at the location where the implantation procedure occurs.

Figure 12:
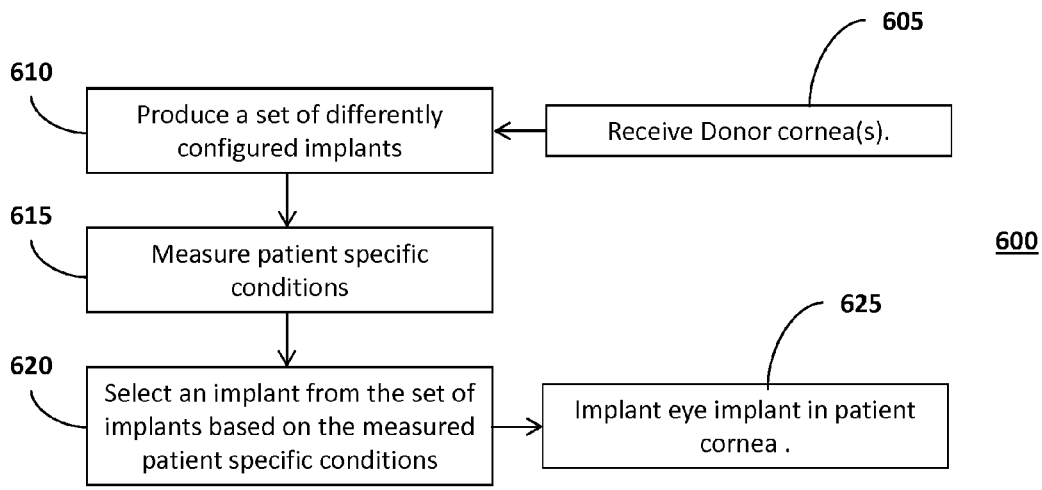
FIG. 12 illustrates another example procedure for processing corneal tissue to produce an eye implant, according to aspects of the present invention.

To further illustrate, FIG. 12 shows an exemplary flowchart of a procedure 600 according to some embodiments. In step 605, one or more donor corneas 50 are received. At step 610, a set of differently configured eye implants 10 (e.g., having different shapes, sizes, etc.) is produced, for example, according to the procedure 500 described above. At step 615, the patient specific information is obtained by measuring the patient specific conditions (e.g., via a patient-measurement device configured to make aberration wavefront measurements, corneal topography measurements, pachymetry measurements, etc.). At step 620, an eye implant 10 is selected from the set of eye implants 10 based on the patient specific information obtained in step 615. At step 625, the selected eye implant 10 is implanted in the patient's cornea (e.g., according to the implantation procedures 100, 300 described above).

In other embodiments, the patient specific information can be obtained first and then the eye implant 10 can be custom manufactured according to the patient specific information. For example, the eye implant 10 can be produced with a size and shape that is based on the measured patient specific information to account for a required refractive correction, a desired change in the anterior corneal surface 26, one or more irregularities of the patient's cornea 16, the surface profile of the stromal bed 24 or outer portion 28 of the cornea 16 at which the implant 10 will be implanted (i.e., the implantation site), removed portions of the epithelium 30 to facilitate regrowth thereof, etc. The patient specific information can be received, processed, and utilized before, during, and/or after any of the steps of the procedure 500 to produce the custom manufactured implant 10.

Figure 13:
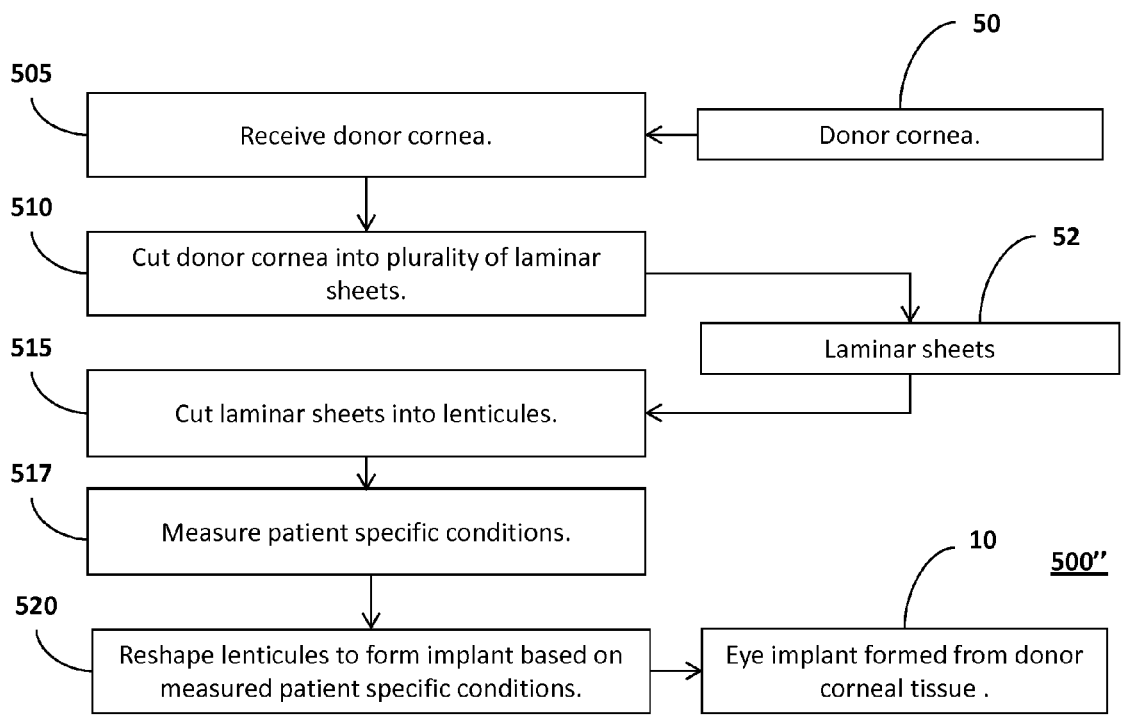
FIG. 13 illustrates another example procedure for processing corneal tissue to produce an eye implant, according to aspects of the present invention.

For example, FIG. 13 illustrates one non-limiting example of a flowchart for a procedure 500" for producing an implant 10 according to such embodiments. As shown in FIG. 13, the steps of the procedure 500" include the steps of the procedure 500 described and illustrated with respect to FIG. 8 and an additional step 517. In step 517, the patient specific information is obtained by measuring the patient specific conditions (e.g., via a patient-measurement device configured to make aberration wavefront measurements, corneal topography measurements, pachymetry measurements, etc.). Then at step 520, the lenticules 54 are reshaped based on the measured patient specific information to form an eye implant 10 customized to the specific conditions of the patient.

According to alternative aspects of the present disclosure, the procedure 500 can be modified and include additional steps such that an implant blank is produced at step 520, which is subsequently reshaped to complete the implant 10 in an additional step according to the measured patient specific information. In other words, the procedure 500 can include one or more additional steps that reshape the donor corneal tissue after step 520. For example, the implant blanks can be mass produced and shipped to surgeons or local processing locations such that the customized implants 10 are finally produced at a location and/or time more proximate to the time and location of the implantation procedure.

Figure 14:
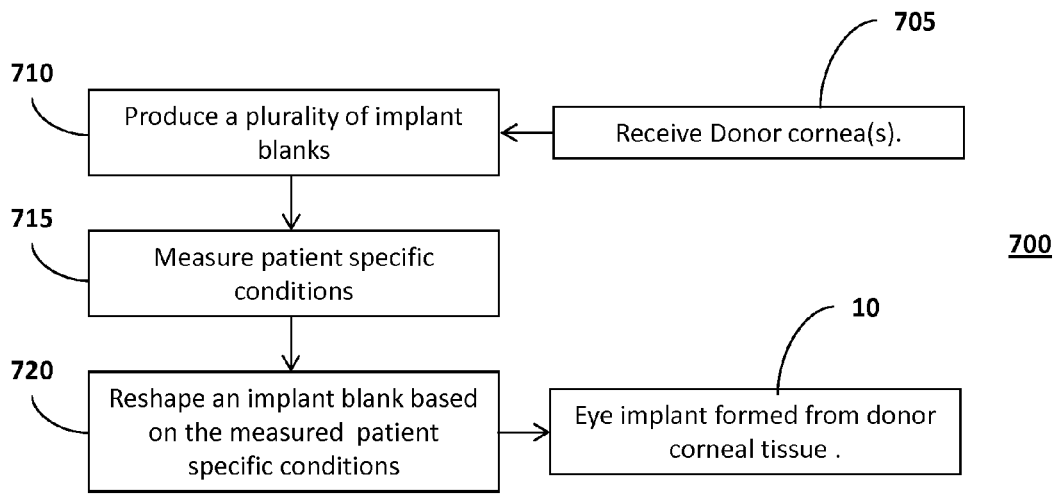
FIG. 14 illustrates another example procedure for processing corneal tissue to produce an eye implant, according to aspects of the present invention.

FIG. 14 illustrates a one non-limiting example of a flowchart for a procedure 700 of producing an eye implant 10 according to such aspects of the present disclosure. In step 705, one or more donor corneas 50 are received. At step 710, a plurality of implant blanks are produced, for example, according to the procedure 500 described above. At step 715, the patient specific information is obtained by measuring the patient specific conditions (e.g., via a patient-measurement device configured to make aberration wavefront measurements, corneal topography measurements, pachymetry measurements, etc.). At step 720, an eye implant 10 is produced from one of the plurality of implant blanks based on the patient specific information obtained in step 715.

Figure 15:
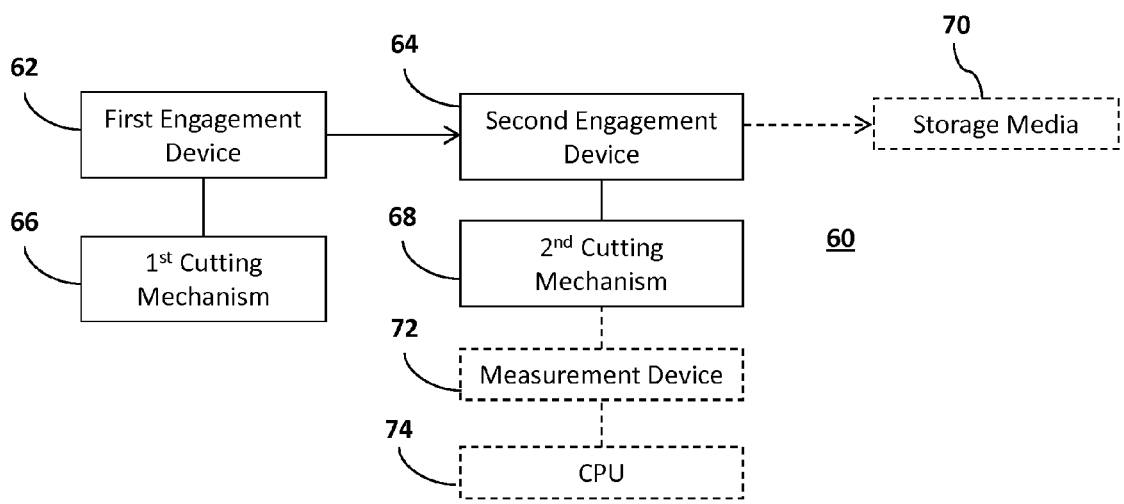
FIG. 15 illustrates an example system for processing corneal tissue to produce an eye implant, according to aspects of the present invention.

Referring now to FIG. 15, a schematic diagram is shown for an exemplary system 60 for manufacturing a plurality of eye implants 10 according to aspects of the present disclosure. As shown in FIG. 15, the system 60 can include a first engagement device 62, a second engagement device 64, a first cutting mechanism 66, and a second cutting mechanism 68. The first engagement device 62 is configured to engage a donor cornea 50 and allow the first cutting mechanism 66 to cut the donor cornea 50 into one or more laminar sheets 52, as described above. The first cutting mechanism 66 can include one or more lasers (e.g., femtosecond lasers and/or excimer lasers), blades, mechanical keratomes, and/or other cutting mechanisms configured to cut the donor cornea 50 into the one or more laminar sheets 52. The second engagement device 64 is configured to receive the laminar sheet(s) 52 from the first engagement device 62 and, thereby, engage the laminar sheet(s) 52 so as to allow the second cutting mechanism 68 to cut and reshape the lenticules 54 to form the eye implants 10. The second cutting mechanism device 68 can also include one or more lasers (e.g., femtosecond lasers and/or excimer lasers), blades, mechanical keratomes, and/or other cutting mechanisms configured to cut lenticules 54 from the laminar sheets 52 and reshape the lenticules 54 to form the implants 10. It is contemplated that, in some embodiments, the first cutting mechanism 66 and the second cutting mechanism 68 can be the same device(s), while in other embodiments, the first cutting mechanism 66 can be separate from the second cutting mechanism 68. Advantageously, the exemplary system 60 allows for a multi-stage procedure for manufacturing a plurality of eye implants 10 from a single donor cornea 50 according to aspects of the present disclosure.

The system 60 can optionally also include a storage media 70, a patient-measurement device 72, and/or a cross-linking system (not shown) as described above. As will be described in further detail below, the system 60 can optionally also include a controller 74 to control and automate aspects of the procedures described herein.

Figure 16A:
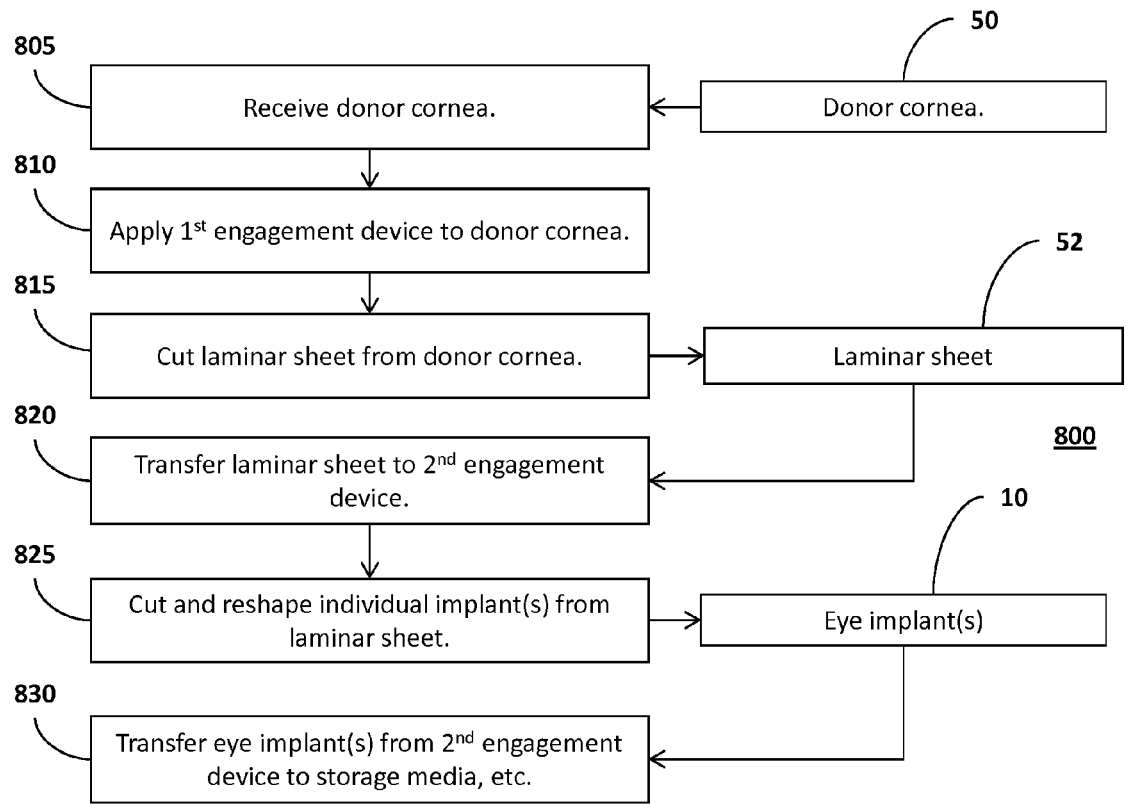
FIG. 16A illustrates yet another example procedure for processing corneal tissue to produce an eye implant, according to aspects of the present invention.
Figure 16B:
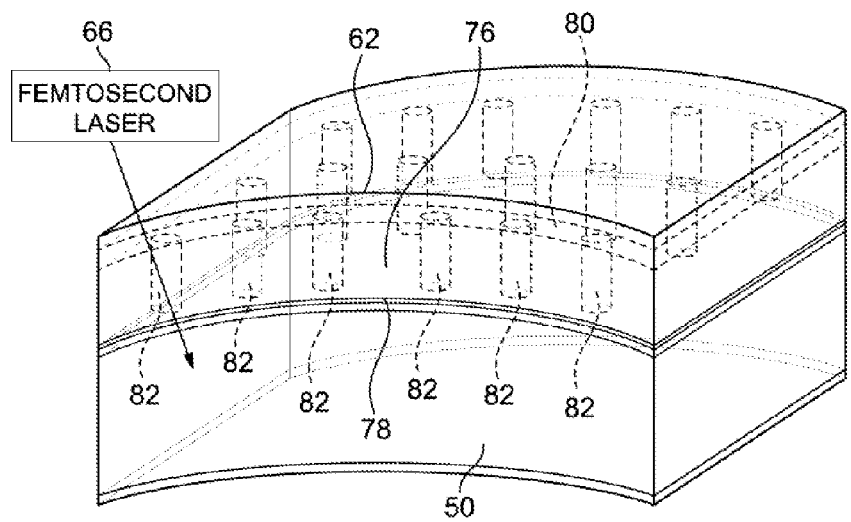
FIG. 16B illustrates an aspect of the procedure of FIG. 16A, according to aspects of the present invention.

Referring to FIG. 16A, yet another example procedure 800 for processing a donor cornea 50 is illustrated. In step 805, a donor cornea 50 is received. In step 810, the first engagement device 62 as shown in FIG. 16B is employed to allow the first cutting mechanism 66 to cut the donor cornea 50 in step 810. The first engagement device 62 includes a body 76 with a surface 78 that engages the donor cornea 50. The surface 78 may be contoured to cover or otherwise accommodate the general shape of donor corneas 50. In the illustrated example, the surface 78 of the first engagement device 62 has a concave contour so as to engage an anterior surface 56 of the donor cornea 50; however, it is contemplated that, according to alternative aspects, the surface 78 can have a convex contour so as to engage a posterior surface 58 of the donor cornea 50. According to some embodiments, the first engagement device 62 can be configured to hold an entire donor eye, which includes the donor cornea 50 and other features of the donor eye. According to other embodiments, the first engagement device 62 can hold only the donor cornea 50 or a portion thereof. For example, the surface 78 can form a mandrel for stably holding the donor cornea 50 (or donor eye).

In FIG. 16B, the first engagement device 62 includes one or more passageways 80 that are coupled to a vacuum source (not shown). A plurality of corresponding vacuum ports 82 leading from the one or more passageways 80 are disposed along the surface 78 to apply a vacuum to the donor cornea 50. The vacuum holds the donor cornea 50 in stable engagement against the surface 78. In some embodiments, the first engagement device 70 can also applanate the donor cornea 50. According to some aspects, the first engagement surface 78 can be made from a ceramic or a metal material that has been micro-drilled to form the ports 82. For example, in the surface 78 can have a flatter contour than the donor cornea 50 such that the vacuum causes the donor cornea 50 to applanate. It is contemplated that, according to additional and/or alternative aspects, other means of applanating the donor cornea 50 can be employed such as, for example, by applying a pressure to a surface of the donor cornea 50 that is not engaged with the surface 78 of the first engagement device 62 (e.g., the posterior surface of the donor cornea 50 in FIG. 16B).

With the donor tissue 50 held stably at the surface 78, the first cutting mechanism 66 can precisely cut the laminar sheet 52 from the donor cornea 50 in step 815. In the example illustrated in FIG. 16B, the first cutting mechanism 66 is a femtosecond laser that cuts one or more laminar sheets 52 from the donor cornea 50; however, as described above, the first cutting mechanism 66 can additionally and/or alternatively include other devices such as, for example, an excimer laser and/or a razor blade.

As described above, each of the one or more laminar sheets 52 may have a thickness of approximately 10 µm to approximately 50 µm. In some cases, the laminar sheet(s) 52 may be shaped to be plano convex. In other cases, the laminar sheet(s) 52 may be shaped to be bi-convex. It is contemplated that other shapes can be formed such as, for example, meniscus, etc. Where the first cutting mechanism 66 employs a femtosecond laser or the like, the body 76 of the first engagement device 62 may be formed at least partially from glass, plastic, or other material that allows the laser to pass through the first engagement device 62 and cut the donor cornea 50 while the first engagement device 62 engages the donor cornea 50. According to additional and/or alternative aspects, the first cutting mechanism 66 can cut the laminar sheet(s) 52 from the donor cornea 50 without passing through the body 76 or any other part of the first engagement device 62 (e.g., at one or more angles generally parallel to the contour of the surface 78). According still other additional and/or alternative aspects, the laminar sheet(s) 52 are cut from the section of the donor cornea 50 disposed along the surface 78, so that a laminar sheet 52 is held by the first engagement device 62 via vacuum ports 82 and can be extracted from the remaining donor cornea 50.

In step 820, the laminar sheet 52 is transferred from the first engagement device 62 to the second engagement device 64. For example, the first cutting mechanism 66 can be configured to cut the a laminar sheet 52 from the side of the donor cornea 50 opposite the surface 78 such that each cut laminar sheet 52 is transferred to the second engagement device 64 before cutting the next laminar sheet 52 from the side of the donor cornea 50 opposite the surface 78.

Figure 16C:
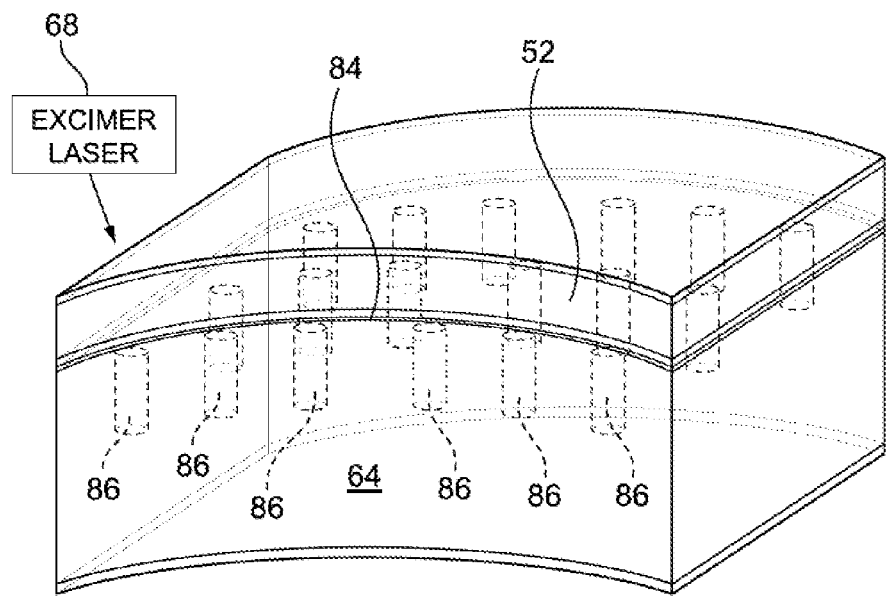
FIG. 16C illustrates another aspect of the procedure of FIG. 16A, according to aspects of the present invention.

FIG. 16C illustrates an exemplary second engagement device 64 according to some aspects of the present disclosure. The second engagement device 64 includes a second engagement surface 84 that receives the laminar sheet 52. A plurality of corresponding vacuum ports 86 coupled to a vacuum source (not shown) are disposed along the second engagement surface 84 to apply a vacuum to the laminar sheet 52. For example, the second engagement surface 84 can be made from a ceramic or a metal material that has been micro-drilled to form the ports 86. According to some aspects of the present disclosure, the first engagement device 62 and the second engagement device 64 can be configured to directly transfer one or more laminar sheets 52 from the first engagement device 62 to the second engagement device 64. For example, the first engagement device 62 may release the laminar sheet 52 to the second engagement device 64 by deactivating the vacuum supplied via vacuum ports 82. At the same time, vacuum is supplied to vacuum ports 86 to hold the laminar sheet 52 against the second engagement surface 84 of the second engagement device 64. The approximately simultaneous deactivation and activation of the vacuums of the first engagement device 62 and the second engagement device 64, respectively, can be controlled by the controller 74 (e.g., in response in response to signals generated by the controller 74) or manually controlled.

According to alternative aspects of the present disclosure, the laminar sheet(s) 52 can be transferred from the first engagement device 62 to the second engagement device 64 via an intermediary device such as, for example, a robotic arm controlled by the controller 74. The deactivation and/or activation of the vacuums of the first engagement device 62 and the second engagement device 64 can be respectively timed and controlled (e.g., manually or via the controller 74) with respect to the movements of the intermediary device.

With the laminar sheet 52 held stably at the second engagement surface 84, the same cutting mechanism 66 or a different cutting mechanism 68 (e.g., including an excimer laser in the illustrated example of FIG. 16C) is employed in step 825. The second cutting mechanism 68 forms one or more individual implants 10 having any desired shapes, dimensions, contours, etc., from the lenticules 54 cut from the laminar sheet 52. For example, the second cutting mechanism 68 cuts and/or reshapes one or more lenticules 54 to form individual implant(s) 10 to desired outer diameters (e.g., approximately 7 mm).

The second engagement device 64 is shaped, contoured, and otherwise configured to accommodate the operations of step 825. In some embodiments, the second engagement device 64 may be shaped like a ball with contours at the second engagement surface 84 that sufficiently accommodate the shape of the laminar sheet 52. For example, the second engagement surface 84 may have specific contours that accommodate a laminar sheet 52 that is bi-convex, plano-convex, and/or meniscus.

As described above with respect to the first engagement device 62, the second engagement device 64 can be formed at least partially from glass, plastic, or other material that allows the excimer laser 68 to pass through the second engagement device 64 and cut/reshape sections of the laminar sheets 52 while the second engagement device 64 engages the laminar sheet 52. In this way, the second engagement device 64 and the second cutting mechanism 68 can be configured to facilitate cutting and/or reshaping of both the front surface 14 and the back surface 12 of the resulting implants 10 according to some aspects of the present disclosure. The second cutting mechanism 68 can be configured to move relative to the stationary surface 84 and the engaged laminar sheet 52, the surface 84 and the engaged laminar sheet 52 can be configured to move relative to the stationary second cutting mechanism 68, and/or both the surface 84 and the second cutting mechanism 68 can be configured to move relative to each other in up to six degrees of freedom (i.e., left, right, up, down, roll, pitch, and/or yaw). As such, the position, orientation, and alignment of the second cutting mechanism 68 relative to laminar sheet 52 can be dynamically adjusted to produce the eye implants 10 having any shape, contour, configuration, etc. required for maximum success in correcting a patient's vision. Moreover, such freedom of movement allows for more extensively customizable implants 10 according to patient specific conditions (e.g., as indicated by patient specific information received from a patient-measurement device 72 as described above). However, in other instances, the second engagement device 64 and the second cutting mechanism 68 can be configured to provide movement in fewer than six degrees of freedom. According to additional and/or alternative embodiments, the second cutting mechanism 68 can include a plurality of cutting mechanisms 68. For example, one second cutting mechanism 68 can be configured to form the front surface 14 of the implant 10 and another second cutting mechanism 68 can be configured to form the back surface 12 of the implant 10. Optionally, micro-marks may be cut into the implant(s) 10 to indicate top, bottom, and/or axis orientations.

Once the implant(s) 10 are formed in step 825, the implant(s) 10 are transferred in step 830 to the storage media 70 and possibly directly to a delivery tool (not shown). In some embodiments, machine vision may be employed to identify the individual implant(s) 10 and a picking device can pick the individual implant(s) 10 from the second engagement device 64, e.g., with a vacuum. The second engagement device 64 may deactivate the vacuum along the entire surface 84 or at selected sections to release the implant(s) 10.

Figure 17:
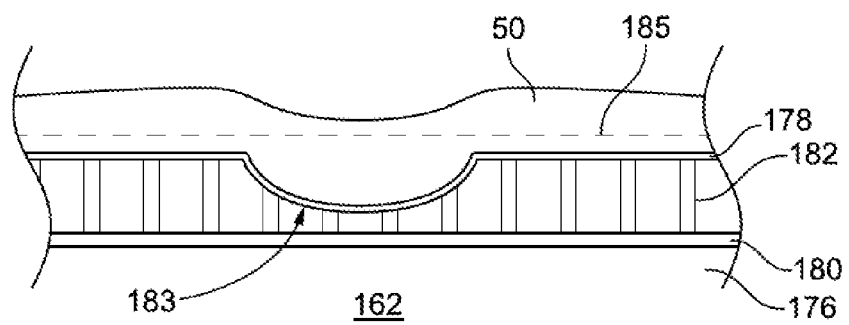
FIG. 17 illustrates another example system for processing corneal tissue to produce an eye implant, according to aspects of the present invention.

As described above, aspects of the procedures described herein can be performed under automated control. FIG. 17 illustrates an exemplary system 60' for manufacturing the eye implants 10 under such automated control. The system 60' can include one or more controllers 74 communicatively coupled to the first engagement device 62, the second engagement device 64, the first cutting mechanism 66, the second cutting mechanism 68, the storage media 70, the patient-measurement device 72, a cross-linking system 92, and/or an intermediary device 94 for transferring the donor cornea 50, the laminar sheets 52, the lenticules 54, and/or the implants 10 at various stages of the manufacturing procedures described herein. As a non-limiting example, in some embodiments, the topography (or other patient specific information) obtained from examination of an individual patient (e.g., via a patient-measurement device 72) may be used to program the process for forming an implant 10. For example, the excimer laser 68 of example 800 may be guided by the topography when it forms the implants 10 in step 825. The optional micro-marks can assist in forming the implants 10 under such automated control. In some embodiments, the topography may be used to determine the shape that is required to address a surface irregularity in a patient with ectasia or keratoconus, e.g., an inverse shape that compensates for the irregularity to give the cornea a more regular shape.

As described above, for example, with respect to FIG. 11, the back surface 12 of the implant 10 can be formed while the laminar sheet 52 is cut from the donor cornea 50. According to some aspects of the present disclosure, the shape of the back surface 12 can be formed by only by the relative movement of the first cutting mechanism 66 and the first engagement device 62. However, according to additional and/or alternative aspects of the present disclosure, the first engagement device 62 can be configured to assist in forming a desired back surface 12 while the laminar sheet 52 is cut from the donor cornea. For example, according to aspects of the present disclosure, the first engagement surface 62 can be provided with a shape that determines, at least in part, the profile of the back surface 12 when the laminar sheet 52 is cut from the donor cornea 50.

FIG. 17 illustrates a partial cross-sectional view of another exemplary first engagement device 162 that is configured to facilitate formation of the back surface 12 as the laminar sheet 52 is cut from the donor cornea 50. As shown in FIG. 17, the first engagement device 162 includes a body 176, a first engagement surface 178, a plurality of passageways 180, and a plurality of vacuum ports 182, which are similar to the corresponding features illustrated and described above for the first engagement device 62 of FIG. 16B. While the first engagement device 62 of FIG. 16B includes a first engagement surface 78 having a convex shape that generally corresponds to the shape of the donor cornea 50, the first engagement surface 178 of the first engagement device 162 shown in FIG. 17 defines a cavity 183 (i.e., a concave region). As shown in FIG. 17, the vacuum force applied via the vacuum ports 82 causes a portion of the donor cornea 50 to be captured within the cavity 183. Accordingly, when the first cutting mechanism 66 is applied to the donor cornea 50 (e.g., along the exemplary cutting line 185), the resulting laminar sheet 52 is thicker in the region of the cavity 183. Thus, the shape of the cavity 183 can assist in defining the shape of the cut laminar sheet 52. With proper selection of the cavity 183 geometry, a new curvature can be imparted to the laminar sheet 52.

While in the example illustrated and described for FIG. 17, the exemplary cutting line 185 is shown as a planar cut through the donor cornea 50, it should be understood that, according to alternative aspects, the first cutting mechanism 66 can make non-planar cuts through donor cornea 50 while it is engaged with the first engagement surface 178. Additionally, it should be understood that the shape of the first engagement surface 178 illustrated in FIG. 17 is merely one example and that other shapes can be employed including, for example, concave shapes, convex shapes, a flat shape, spherical shapes, aspheric shapes, etc. While a concave shape may assist in forming a laminar sheet 52 having a more flat profile for the back surface 12, a convex shape may assist in forming a laminar sheet 52 having a more steep profile for the back surface 12. It should be understood that while the shape of the first engagement surface 178 is shown in two-dimensions in FIG. 17, the shape of the first engagement surface 178 is a three-dimensional shape and, thus, the concave, convex, flat, etc. portion(s) of the first engagement surface 178 are three-dimensional shapes.

Additionally, in the example illustrated and described for FIG. 17, the laminar sheet 52 is produced from a lowermost portion of the donor cornea 50 (i.e., the portion of the donor cornea 50 in contact with the first engagement surface 178). To continue the procedure for processing the donor cornea 50 to form the implant 10, the remaining portion of the donor cornea 50 (i.e., the portion of the donor cornea 50 above the cutting line 185 in FIG. 17) can be removed from the cut laminar sheet 52, which is still engaged with the first engagement surface 178, and then the laminar sheet 52 can be transferred to the second engagement device 64, as described above. In one non-limiting example, to remove the remaining portion of the donor cornea 50, the intermediary device 94 can be employed. According to some aspects, once the laminar sheet 52 is transferred to the second engagement device 64, the remaining portion of the donor cornea 50 can be again placed on the first engagement surface 178 so that the next laminar sheet 52 can be cut. It should be understood that these aspects of an example procedure for processing the donor cornea 50 can also be utilized for the first engagement device 62 illustrated and described for FIG. 16B.

According to some aspects, the first engagement device 162 can be utilized with the same first engagement surface 178 for each laminar sheet 52 cut from the donor cornea 50; however, according to additional and/or alternative aspects, a different first engagement surface 178 can be utilized for one or more of the laminar sheets 52 cut from the same donor cornea 50. For example, the first engagement surface 178 employed on the first engagement device 162 can be one of a plurality of interchangeable first engagement surfaces 178, each having a different surface profile or geometry. In other words, the first engagement surface 178 can be a modular component that can be swapped out on the first engagement device 162. In this way, a plurality of laminar sheets 52 having different shapes can be cut from a single donor cornea 50. Additionally, because the shape of the first engagement surface 178 can affect the shape of the remaining donor cornea 50 after a laminar sheet 52 has been cut, a different first engagement surface 178 may be employed to account for the changed shape of the remaining donor cornea 50 before cutting the next laminar sheet 52 from the donor cornea 50.

As described above, the first engagement device (e.g., the first engagement devices 62, 162) and the second engagement device (e.g., the second engagement device 64) can be configured to apply a vacuum to the donor cornea 50 and/or the laminar sheets 52. According to some aspects of the present disclosure, the vacuum can be applied to a gas in contact with the donor cornea 50 and/or the laminar sheets 52 via the vacuum ports 82, 86. According to additional and/or alternative aspects of the present disclosure, the vacuum can be applied to a fluid in contact with the donor cornea 50 and/or the laminar sheets 52 via the vacuum ports 82, 86. For example, as described above, one or more of the steps of the manufacturing processes described herein can be performed with the donor tissue 50, the laminar sheets 52, and/or the lenticules 54 submerged in a fluid according to some aspects of the present disclosure. In such embodiments, the vacuum can be applied to the fluid in which the donor tissue 50, the laminar sheets 52, and/or the lenticules 54 are submerged.

Figure 18:
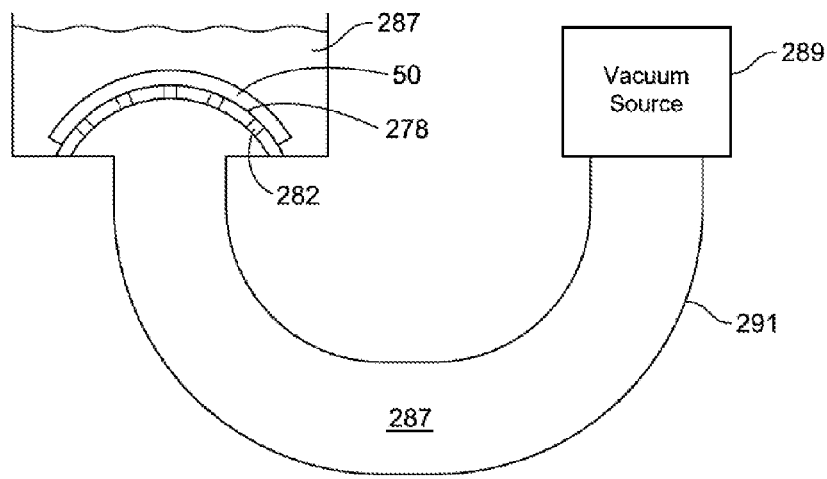
FIG. 18 illustrates another example system for processing corneal tissue to produce an eye implant, according to aspects of the present invention.

FIG. 18 illustrates an exemplary first engagement device 262 configured to submerge the donor cornea 50 in a fluid 287 while the laminar sheet(s) 52 are cut from the donor cornea 50. The first engagement device 262 includes a fluid reservoir 289 in which the first engagement surface 278 is located. The fluid reservoir 289 is in fluid communication with a fluid conduit 291 via the ports 282 in the first engagement surface 278. The fluid conduit 291 is communicatively coupled to the first engagement surface 278 at one end and a vacuum source 293 at the other end. The fluid conduit 291 is configured to contain the fluid 287. Accordingly, when the vacuum source 293 applies a vacuum pressure to the fluid 287 in the fluid conduit 291, the donor cornea 50 is held stably against the first engagement surface 278 due to the pressure applied by the fluid 287 via the ports 282. Advantageously, applying the vacuum pressure to the fluid 287 in this manner maintains the donor cornea 50 in contact with the fluid 287 while the laminar sheet(s) 52 are cut from the donor cornea 50. It should be understood that a similar system can be employed for the second engagement mechanism 64 as well (e.g., the second engagement mechanism 64 can include a fluid 287, a fluid reservoir 289, a fluid conduit 291, and a vacuum source 293). As shown in FIG. 18, the fluid conduit 291 has a generally U-shaped configuration; however, it should be understood that, according to additional and/or alternative aspects of the present disclosure, the fluid conduit 291 can be differently shaped.

Figure 19:
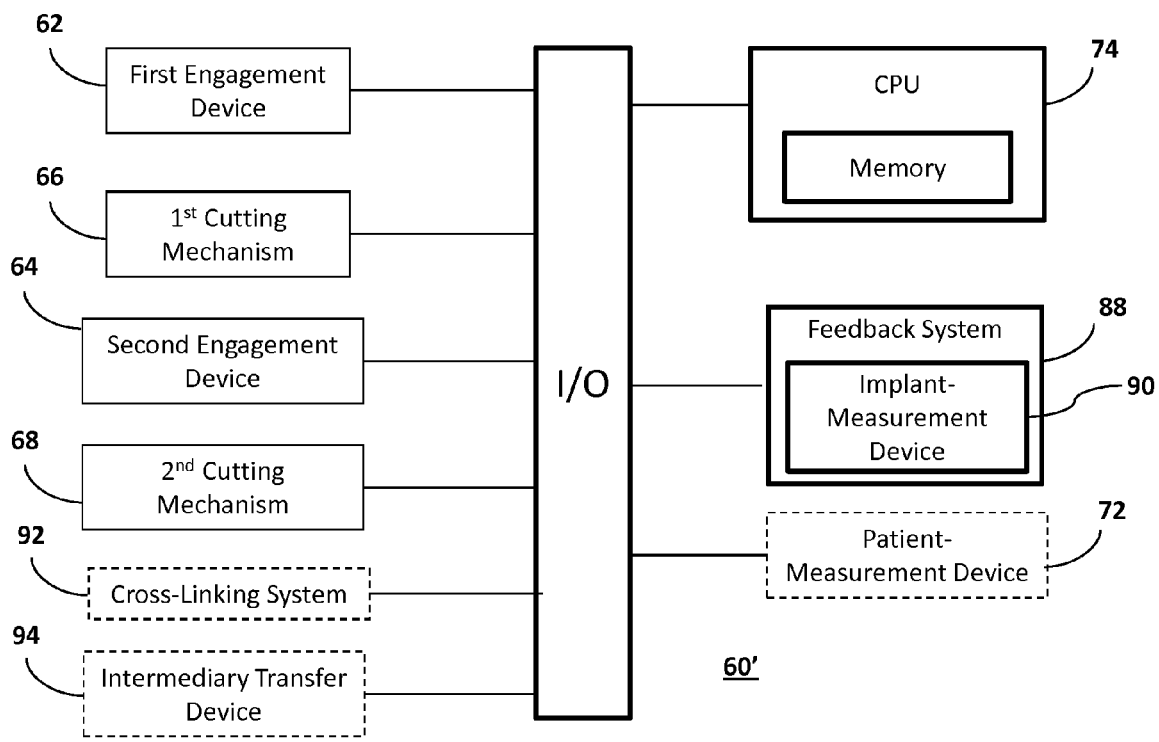
FIG. 19 illustrates yet another example system for processing corneal tissue to produce an eye implant, according to aspects of the present invention.

According to additional and/or alternative aspects, the system 60 can further include a feedback system 88 as shown, for example, in FIG. 19. The feedback system 88 can include an implant-measurement device 90 that is configured to measure the size, shape, and/or thickness of the donor cornea 50, the laminar sheets 52, the lenticules 54, and/or the implants 10 at one or more stages of the procedures described above. The feedback system 88 can include and/or be communicatively coupled to the controller(s) 74 so as to provide feedback information that can be utilized to improve and/or verify the quality of the implants 10 produced from the procedures described herein. For example, the feedback system 88 can be utilized to verify whether an implant 10 was actually produced with the predetermined shape and size it was intended to have. Additionally, for example, after a laminar sheet 52 has been cut from the donor cornea 50 at step 510, the feedback system can provide an indication as to the thickness of the laminar sheet 52 so that the correct amount of reshaping can be performed at step 520 to achieve an implant 10 with a desired predetermined thickness.

FIGS. 8, 11, 12, 13, 14, and 16A described by way of example above, represent exemplary algorithms that correspond to at least some instructions executed by one or more controllers CPU 74 in FIG. 15 to perform the above described functions associated with the described concepts. It is also within the scope and spirit of the present concepts to omit steps, include additional steps, and/or modify the order of steps presented above.

As described above, according to some aspects of the present disclosure, some or all of the steps of the above-described and illustrated procedures can be automated under the control of a controller. Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

I claim:

1. A method of making an implant for correcting vision impairment, comprising:
receiving a donor corneal tissue, the donor corneal tissue including stromal tissue between an anterior surface and a posterior surface;
cutting a plurality of lamellar sheets from the stromal tissue, wherein cuts are made between the posterior surface and the anterior surface and parallel to the posterior surface or the anterior surface to define surfaces of the lamellar sheets, and the lamellar sheets are defined by lamellar layers in the stromal tissue, parallel to the posterior surface or the anterior surface;
cutting a plurality of lenticules from the lamellar sheets; and
selecting at least one of the lenticules to be reshaped to form an implant having a shape and size configured for a predetermined refractive correction.

2. The method of claim 1, further comprising reshaping the at least one of the lenticules to form an implant having a shape and size configured for a predetermined refractive correction.

3. The method of claim 2, wherein the at least one of the lenticules is reshaped prior to the lenticule being cut from the lamellar sheets.

4. The method of claim 2, wherein the reshaping includes reshaping a surface of the at least one of the lenticules to have a profile based on a surface profile of an implantation site of a cornea.

5. The method of claim 1, wherein the lamellar sheets are cut from the stromal tissue by a femtosecond laser.

6. The method of claim 2, wherein the at least one of the lenticules is reshaped to form the implant using an excimer laser.

7. The method of claim 1, wherein the cutting the lamellar sheets from the stromal tissue is performed in a controlled environment that maintains the implant at a state of hydration that generally corresponds to a state of hydration of a recipient cornea.

8. The method of claim 1, wherein selecting at least one of the lenticules includes selecting a plurality of the lenticules to be reshaped to form a plurality of implants, wherein the plurality of implants are configured to provide a plurality of different refractive corrections.

9. The method of claim 1, further comprising:
engaging the donor corneal tissue with a first engagement device, the lamellar sheets being cut from the stromal tissue while the donor corneal tissue engages the first engagement device; and
after the cutting of each lamellar sheet from the stromal tissue, transferring the lamellar sheet from the first engagement device to a second engagement device, one or more of the lenticules being cut from the lamellar sheet while the lamellar sheet is engaged by the second engagement device.

10. The method of claim 9, wherein the first engagement device includes a first engagement surface for engaging the donor corneal tissue, the first engagement surface includes a cavity and the first engagement device is configured to apply a vacuum pressure to the donor corneal tissue to capture a portion of the donor corneal tissue within the cavity while the lamellar sheets are cut from the stromal tissue.

11. The method of claim 10, wherein the vacuum pressure is applied to the donor corneal tissue via a fluid in contact with the donor corneal tissue.

12. The method of claim 9, further comprising applanating the donor corneal tissue using the first engagement device while the lamellar sheets are cut from the stromal tissue.

13. The method of claim 2, further comprising determining the topography of a cornea, the plurality of lenticules being cut from the lamellar sheets and the at least one of the lenticules being reshaped to form the implant based on the determined topography of the cornea.

14. The method of claim 1, further comprising applying a cross-linking agent to the donor corneal tissue and activating the cross-linking agent to strengthen the donor corneal tissue.

15. The method of claim 1, further comprising sterilizing the implant.

* * * * *